United States Patent
Vitullo et al.

(10) Patent No.: US 10,258,774 B2
(45) Date of Patent: Apr. 16, 2019

(54) SMART 3-WAY VALVE WITH HIGH AND LOW PRESSURE SENSING

(71) Applicants: Jeffrey Vitullo, Reading, PA (US); David T. Rowe, Sinking Spring, PA (US); John Victor, Kunkletown, PA (US)

(72) Inventors: Jeffrey Vitullo, Reading, PA (US); David T. Rowe, Sinking Spring, PA (US); John Victor, Kunkletown, PA (US)

(73) Assignee: Teleflex Medical Incorporated, Morrisville, NC (US)

( * ) Notice: Subject to any disclaimer, the term of this patent is extended or adjusted under 35 U.S.C. 154(b) by 343 days.

(21) Appl. No.: 14/067,573

(22) Filed: Oct. 30, 2013

(65) Prior Publication Data

US 2014/0121515 A1 May 1, 2014

Related U.S. Application Data

(60) Provisional application No. 61/720,569, filed on Oct. 31, 2012.

(51) Int. Cl.
*A61M 25/10* (2013.01)
*A61M 5/00* (2006.01)
(Continued)

(52) U.S. Cl.
CPC .... *A61M 25/10185* (2013.11); *A61M 39/223* (2013.01); *A61M 25/104* (2013.01);
(Continued)

(58) Field of Classification Search
CPC ........ A61M 25/10185; A61M 25/0097; A61M 25/10187; A61M 25/10188;
(Continued)

(56) References Cited

U.S. PATENT DOCUMENTS

| 489,107 A | 1/1893 | Storz |
|---|---|---|
| 4,609,370 A | 9/1986 | Morrison |

(Continued)

OTHER PUBLICATIONS

Giridharan et al., Physiological Control of Blood Pumps Using Intrinsic Pump Parameters: A Computer Simulation Study, Artificial Organs, 30: 301-307 (2006) (7 pages).

(Continued)

*Primary Examiner* — Nathan R Price
*Assistant Examiner* — Justin L Zamory
(74) *Attorney, Agent, or Firm* — Baker & Hostetler LLP (57) ABSTRACT

Apparatus and methods are provided for managing delivery of fluid into a vessel. A balloon catheter with a 3-way valve is introduced into an occluded vessel. The 3-way valve permits fluid, such as a contrast dye, to be injected into the vessel lumen. The valve is also configured to permit the balloon portion of the catheter to be inflated by means of the same lumen used to inject the contrast dye into the vessel. Bloodstream pressure can also be measured before and after dilation to confirm the procedure was successful. This apparatus and method provides for a quick, safe, and reliable treatment of an occluded vessel, among other things and works with known and later developed systems.

16 Claims, 8 Drawing Sheets

(51) Int. Cl.
*A61M 39/22* (2006.01)
*A61M 31/00* (2006.01)
*A61M 25/00* (2006.01)

(52) U.S. Cl.
CPC . *A61M 25/10182* (2013.11); *A61M 25/10187* (2013.11); *A61M 25/10188* (2013.11); *A61M 31/005* (2013.01); *A61M 2025/0003* (2013.01)

(58) Field of Classification Search
CPC .......... A61M 25/10182; A61M 25/104; A61M 39/223; A61M 2039/229; A61M 2205/3351; F16K 37/005
See application file for complete search history.

(56) References Cited

U.S. PATENT DOCUMENTS

| | | | |
|---|---|---|---|
| 4,648,630 A | | 3/1987 | Bruch |
| 5,562,614 A | * | 10/1996 | O'Donnell ........ A61M 25/1018 604/65 |
| 5,669,879 A | * | 9/1997 | Duer ................ A61M 25/0108 604/99.04 |
| 5,832,959 A | * | 11/1998 | Szymczakowski ........................ A61M 39/223 137/556 |
| 5,885,217 A | | 3/1999 | Gisselberg et al. |
| 6,336,914 B1 | | 1/2002 | Gillespie, III |
| 6,663,595 B2 | | 12/2003 | Spohn et al. |
| 6,695,816 B2 | | 2/2004 | Cassidy, Jr. |
| 7,128,091 B2 | | 10/2006 | Istre, Jr. |
| 8,043,313 B2 | | 10/2011 | Krolik et al. |
| 8,298,252 B2 | | 10/2012 | Krolik et al. |
| 2002/0143294 A1 | * | 10/2002 | Duchon ................ A61M 5/14 604/131 |
| 2003/0078538 A1 | * | 4/2003 | Neale ................ A61M 25/1018 604/98.01 |
| 2005/0038448 A1 | * | 2/2005 | Chung ................ A61B 17/54 606/131 |
| 2005/0090779 A1 | | 4/2005 | Osypka |
| 2007/0123825 A1 | | 5/2007 | King et al. |
| 2008/0262430 A1 | | 10/2008 | Anderson et al. |
| 2010/0036410 A1 | * | 2/2010 | Krolik ............ A61B 17/22032 606/194 |
| 2010/0204654 A1 | | 8/2010 | Mulholland et al. |
| 2011/0071390 A1 | * | 3/2011 | Liu ........................ A61B 6/481 600/431 |
| 2014/0094777 A1 | | 4/2014 | Watanabe et al. |

OTHER PUBLICATIONS

Bullister et al., Physiologic Control Algorithms for Rotary Blood Pumps Using Pressure Sensor Input, Artificial Organs, 26: 931-938 (2002) (8 pages).

Potkay, J., Long term, implantable blood pressure monitoring systems, Biomedical Microdevices, vol. 10, Issue 3, pp. 379-392 (2008) (14 pages).

Miley et al., Comparison Between Angioplasty Using Compliant and Noncompliant Balloons for Treatment of Cerebral Vasospasm Associated With Subarachnoid Hemorrhage, Neurosurgery, vol. 69, No. 6, pp. 161-168 (2011) (8 pages).

\* cited by examiner

SMART 3-WAY VALVE WITH HIGH AND LOW PRESSURE SENSING

RELATED APPLICATIONS

This application claims priority benefit from U.S. Ser. No. 61/720,569, filed Oct. 31, 2012, entitled "Smart 3-Way Valve with High and Low Pressure Sensing," which is incorporated by this reference herein in its entirety. This application expressly incorporates by reference U.S. Pat. No. 8,043,313, issued Oct. 25, 2011, and U.S. patent application Ser. No. 12/564,892, filed on Sep. 22, 2009, the contents of which are incorporated by this reference as if fully set forth herein, in their entirety, along with U.S. Pat. No. 8,298,252, issued Oct. 30, 2012, along with U.S. patent application Ser. No. 13/644,022 filed on Oct. 3, 2012 and U.S. patent application Ser. No. 13/655,688 filed on Oct. 19, 2012, all owned by a common assignee, along with full Paris Convention priority.

BACKGROUND OF THE DISCLOSURE

Angioplasty (percutaneous transluminal angioplasty (PTA) or percutaneous transluminal coronary angioplasty (PTCA) is a procedure that is used to dilate occluded vessels in the vascular system. The procedure typically consists of multiple steps. First, an introducer sheath is placed in the patient to provide a point of access for catheter placement. Once access has been obtained, sometimes a guiding catheter is placed in to the vessel near the occlusion and injected with an x-ray sensitive dye (contrast) that is to be infused into the blood stream. The contrast can also be injected through the introducer sheath depending on the location of the occlusion relative to the introducer sheath. The farther the distance the more likely a guiding catheter will be used to facilitate localizing the contrast for improved image quality and to minimize the amount of contrast for patient safety.

The contrast is viewed under a fluoroscope as it travels through the blood stream to identify the block or constricted vessel. After the location of the blockage is identified, the guiding catheter is extracted and replaced with an angioplasty balloon catheter used to dilate the vessel. The standard angioplasty balloon catheter is constructed with a high-pressure, non-compliant balloon on the distal tip and a means for inflating the balloon on the proximal end. This catheter is inserted into the introducer sheath and guided into position by radiopaque marker bands on the catheter shaft. Once the catheter is appropriately placed at the point of the blockage, the balloon is inflated at high pressure using an inflation syringe (insufflator) to dilate the vessel. After dilation the catheter is extracted and the guiding catheter is once again placed into the vessel to inject the contrast to confirm the blockage has been fully opened.

Inflation syringes are available, for example, Taut® System One, Teleflex Medical, Research Triangle Park, N.C.; Medflator®, Smiths Medical, St. Paul, Minn.; Basix Compak®, Merit Medical, South Jordan, Utah. Insufflation devices for inflating angioplasty balloons have been described (see, e.g., Miley et al (2011) Neurosurgery. 69:ons161-ons168). Inflation syringe or insufflator may be configured to deliver pressure in the range of 0-25 atmospheres. Processes for delivering inflation media, diagnostic agents, therapeutic agents to a vascular lumen (or other lumen in the body) or to a balloon, by way of syringe and catheter, are disclosed by U.S. Pat. No. 8,043,313 of Krolik et al, and of U.S. Pat. No. 8,298,252 of Krolik et al, where are each incorporated by reference in their entirety. Therapeutic agent can include agent to reduce re-stenosis, such as anti-proliferative drug (see, e.g., U.S. Ser. No. 13/644,022 of Krolik, which is incorporated herein in its entirety).

Some physicians prefer to measure the intravascular pressure before and after the dilatation of the vessel. This measurement can be achieved by using disposable pressure transducers connected to the balloon catheter's inner lumen, which is exposed to the bloodstream. This technique allows for a more precise method of measuring the performance of the angioplasty procedure.

SUMMARY OF THE DISCLOSURE

Briefly stated, the disclosure provides apparatus and methods for managing delivery of fluid into a vessel. A balloon catheter with a 3-way valve is introduced into an occluded vessel. The 3-way valve permits fluid, such as a contrast dye, to be injected into the vessel lumen. The valve is also configured to permit the balloon portion of the catheter to be inflated by means of the same lumen used to inject the contrast dye into the vessel. Bloodstream pressure can also be measured before and after dilation to confirm the procedure was successful. This apparatus and method provides for a quick, safe, and reliable treatment of an occluded vessel, among other things and works with known and later developed systems.

The disclosure provides a valve unit configured for directing a high pressure fluid to a balloon that comprises a balloon lumen, and configured for directing low pressure fluid to a vascular lumen, the valve unit comprising: (i) a 3-way valve operably linked with a high pressure fluid port, a low pressure fluid port, and an exit port; and (ii) a high pressure fluid input port, a low pressure fluid port, and an exit port; wherein the 3-way valve has a first position that is configured to receive the high pressure fluid via the high pressure fluid port, wherein the 3-way valve has a second position that is configured to receive the low pressure fluid via the low pressure fluid port, wherein the 3-way valve is configured to transmit the high pressure fluid to the exit port, and is configured to transmit the low pressure fluid to the exit port; and wherein the valve has a third position that is configured to simultaneously prevent flow of high pressure fluid from the high pressure fluid port to the exit port and flow of low pressure fluid from the low pressure port to the exit port, (iii) a high pressure sensor that detects pressure of the high pressure fluid, wherein the high pressure sensor is segregated from and not exposed to the low pressure fluid; and (iv) a low pressure sensor that detects pressure of the low pressure fluid, wherein the low pressure sensor is segregated from and not exposed to the high pressure fluid.

What is also provided is the above valve unit that does not comprise a balloon.

Also provided is the above valve unit, wherein the balloon is an angioplasty balloon.

What is also embraced, is the above valve unit, wherein the low pressure sensor is located upstream of the 3-way valve, or wherein the high pressure sensor is located upstream of the 3-way valve, or wherein the low pressure sensor is located upstream of the 3-way valve, and the high pressure sensor is located upstream of the 3-way valve.

Moreover, what is also provided is the above valve unit, wherein the low pressure sensor, the high pressure sensor, or both the low pressure sensor and the high pressure sensor are located in the valve body of the 3-way valve.

Further contemplated is the above valve unit, wherein the low pressure fluid comprises a contrast agent, a therapeutic agent, or a contrast agent and a therapeutic agent.

In an embodiment that includes a catheter and longitudinally-moving valve, the present disclosure provides the above valve unit, further comprising: (i) an outer catheter body that comprises a proximal end, a distal end, and an outer catheter body lumen extending between the proximal and distal end, wherein the outer catheter body defines a first longitudinal axis; (ii) an inner catheter body (inner shaft) that resides, at least in part, in the outer catheter body lumen, wherein the inner catheter body defines a second longitudinal axis, and wherein the first longitudinal axis is parallel to the second longitudinal axis, wherein the inner catheter body comprises a proximal end and a distal end, wherein the inner catheter body distal end comprises a longitudinally-moving valve that (A) is capable of forming a sealed contact with the outer catheter body distal end, wherein the sealed contact prevents fluid flow from the outer catheter body lumen to a vascular lumen, and (B) is also capable of forming an unsealed gap with the outer catheter body distal end, wherein the unsealed gap allows fluid flow from the outer body lumen to the vascular lumen; (iii) wherein the inner catheter body distal end comprises an inflation lumen, wherein the inflation lumen comprising a third longitudinal axis that is parallel to the first and second longitudinal axes, wherein the inflation lumen passes through the longitudinally-moving valve, and is configured to allow high pressure fluid to pass through the inflation lumen when the longitudinally-moving valve is in sealed contact with the distal end of the outer catheter body.

Also provided is the above valve unit, further comprising a thumb slide that is operably linked to the 3-way valve, wherein the thumb slide is configured to control the 3-way valve to allow either passage of the high pressure fluid to the exit port, or passage of the low pressure fluid to the exit port.

Moreover, what is also provided is the above valve unit, that comprises a thumb slide that is operably linked to a longitudinally-moving valve, wherein proximal-to-distal movement of thumb slide, opens longitudinally-moving valve, and distal-to-proximal movement of thumb slid closes longitudinally-moving valve.

In an embodiment that includes a thumb slide that can control the 3-way valve, the longitudinally-moving valve, or both, the present disclosure provides the above valve unit that comprises a thumb slide, wherein the thumb slide is: (i) operably linked to the 3-way valve, wherein the thumb slide is configured to control the 3-way valve to allow either passage of the high pressure fluid to the exit port, or passage of the low pressure fluid to the exit port, and (ii) operably linked to the longitudinally-moving valve, wherein proximal-to-distal movement of thumb slide, opens longitudinally-moving valve, and distal-to-proximal movement of thumb slid closes longitudinally-moving valve.

Also provided is the above valve unit, further comprising a low pressure fluid syringe, an insufflator, or both a low pressure fluid syringe and an insufflator. Also provided is the above valve unit, further comprising a display that is capable of displaying the pressure detected by the low pressure sensor and by the high pressure sensor. Further provided is the above valve unit, further comprising the high pressure fluid, the low pressure fluid, or both the high pressure fluid and the low pressure fluid.

Also provided is the above valve unit, that is configured for controlling the flow and transmission of a high pressure fluid that is under a pressure of at least 30 atmospheres (atm). Moreover, what is also provided is above valve unit, further comprising an angioplasty balloon that is operably linked with the high pressure fluid port.

In another aspect, what is provided is above valve unit, further comprising an angioplasty balloon that is operably linked with the high pressure port and with the inflation lumen.

Also embraced, is above valve unit, further comprising: (i) an insufflator or high pressure syringe, and (ii) a low pressure syringe.

In a method of use embodiment, the disclosure provides a method for dilating a vessel to treat an occlusion of the vessel, the method comprising the steps of: providing an apparatus comprising the 3-way valve unit that is described above, wherein the 3-way valve unit further comprises an angioplasty balloon operably linked with the high pressure port and inflation lumen, and wherein the angioplasty balloon is downstream of the inflation lumen, introducing the inner catheter body (inner shaft) into the vessel; injecting a low pressure fluid that comprises a contrast dye through the inflation lumen into the vessel; directing the inner catheter body (inner shaft) to the occlusion; and inflating the balloon by injecting a high pressure fluid that is an inflation fluid through the inflation lumen to dilate the vessel at the occlusion.

Also provided is the above method, wherein all of the steps can be performed without needing to remove any portion of the apparatus from the vessel.

Another method that is provided, is a method for dilating a vessel to treat an occlusion of the vessel, the method comprising the steps of: Step 1. Providing a valve unit configured for directing a high pressure fluid to a balloon that comprises a balloon lumen, and configured for directing low pressure fluid to a vascular lumen, the valve unit comprising: (i) a 3-way valve operably linked with a high pressure fluid port, a low pressure fluid port, and an exit port; and (ii) a high pressure fluid input port, a low pressure fluid port, and an exit port; wherein the 3-way valve has a first position that is configured to receive the high pressure fluid via the high pressure fluid port, wherein the 3-way valve has a second position that is configured to receive the low pressure fluid via the low pressure fluid port, wherein the 3-way valve is configured to transmit the high pressure fluid to the exit port, and is configured to transmit the low pressure fluid to the exit port; and wherein the valve has a third position that is configured to simultaneously prevent flow of high pressure fluid from the high pressure fluid port to the exit port and flow of low pressure fluid from the low pressure port to the exit port, (iii) a high pressure sensor that detects pressure of the high pressure fluid, wherein the high pressure sensor is segregated from and not exposed to the low pressure fluid; (iv) a low pressure sensor that detects pressure of the low pressure fluid, wherein the low pressure sensor is segregated from and not exposed to the high pressure fluid; (v) an outer catheter body that comprises a proximal end, a distal end, and an outer catheter body lumen extending between the proximal and distal end, wherein the outer catheter body defines a first longitudinal axis; (vi) an inner catheter body (or inner shaft) that resides, at least in part, in the outer catheter body lumen, wherein the inner catheter body defines a second longitudinal axis, and wherein the first longitudinal axis is parallel to the second longitudinal axis, wherein the inner catheter body comprises a proximal end and a distal end, wherein the inner catheter body distal end comprises a longitudinally-moving valve that (A) is capable of forming a sealed contact with the outer catheter body distal end, wherein the sealed contact prevents fluid flow from the outer catheter body lumen to a vascular lumen, and (B) is also capable of forming an unsealed gap with the outer catheter body distal end, wherein the unsealed gap allows fluid flow from the outer body lumen to the vascular lumen; (vii) wherein the inner catheter body distal end comprises an inflation lumen, wherein the inflation lumen comprising a third longitudinal axis that is parallel to the first and second longitudinal axes, wherein the inflation lumen passes through the longitudinally-moving valve, and is configured to allow high pressure fluid to pass through the inflation lumen when the longitudinally-moving valve is in sealed contact with the distal end of the outer catheter body, wherein the 3-way valve unit further comprises an angioplasty balloon operably linked with the high pressure port and inflation lumen, and wherein the angioplasty balloon is downstream of the inflation lumen; Step II. Introducing the inner catheter body (inner shaft) into the vessel; Step III. Injecting a low pressure fluid that comprises a contrast dye through the inflation lumen into the vessel; Step IV. Directing the inner catheter body (inner shaft) to the occlusion; and Step V. Inflating the balloon by injecting a high pressure fluid that is an inflation fluid through the inflation lumen to dilate the vessel at the occlusion; wherein all of the steps can be performed without needing to remove any portion of the apparatus from the vessel.

The disclosure also provides the following device. What is provided is a valve unit configured for directing a high pressure fluid to a balloon that comprises a balloon lumen, and configured for directing low pressure fluid to a vascular lumen, the valve unit comprising: (i) a 3-way valve operably linked with a high pressure fluid port, a low pressure fluid port, and an exit port; and (ii) a high pressure fluid input port, a low pressure fluid port, and an exit port; wherein the 3-way valve has a first position that is configured to receive the high pressure fluid via the high pressure fluid port, wherein the 3-way valve has a second position that is configured to receive the low pressure fluid via the low pressure fluid port, wherein the 3-way valve is configured to transmit the high pressure fluid to the exit port, and is configured to transmit the low pressure fluid to the exit port; and wherein the valve has a third position that is configured to simultaneously prevent flow of high pressure fluid from the high pressure fluid port to the exit port and flow of low pressure fluid from the low pressure port to the exit port, (iii) a high pressure sensor that detects pressure of the high pressure fluid, wherein the high pressure sensor is segregated from and not exposed to the low pressure fluid; (iv) a low pressure sensor that detects pressure of the low pressure fluid, wherein the low pressure sensor is segregated from and not exposed to the high pressure fluid; (v) an outer catheter body that comprises a proximal end, a distal end, and an outer catheter body lumen extending between the proximal and distal end, wherein the outer catheter body defines a first longitudinal axis; (vi) an inner catheter body (or inner shaft) that resides, at least in part, in the outer catheter body lumen, wherein the inner catheter body defines a second longitudinal axis, and wherein the first longitudinal axis is parallel to the second longitudinal axis, wherein the inner catheter body comprises a proximal end and a distal end, wherein the inner catheter body distal end comprises a longitudinally-moving valve that (A) is capable of forming a sealed contact with the outer catheter body distal end, wherein the sealed contact prevents fluid flow from the outer catheter body lumen to a vascular lumen, and (B) is also capable of forming an unsealed gap with the outer catheter body distal end, wherein the unsealed gap allows fluid flow from the outer body lumen to the vascular lumen; (vii) wherein the inner catheter body distal end comprises an inflation lumen, wherein the inflation lumen comprising a third longitudinal axis that is parallel to the first and second longitudinal axes, wherein the inflation lumen passes through the longitudinally-moving valve, and is configured to allow high pressure fluid to pass through the inflation lumen when the longitudinally-moving valve is in sealed contact with the distal end of the outer catheter body. What is also provided is the above valve unit that does not comprise a balloon.

Briefly stated, the instant disclosure reduces the number of steps required to complete the angioplasty procedure, among others. A specialized catheter (GPS OATH® available from Teleflex Medical, Inc., Reading, Pa.) utilizes a 3-way injection valve which gives the balloon catheter the ability to inject contrast at the proximal end of the balloon as well as utilize the lumen to inflate the balloon. This advancement significantly reduces procedural time and the amount of contrast required to identify the blockage.

According to embodiments, the 3-way valve allows any catheter to be placed in a vessel in proximity to the occlusion where contrast can be injected into the bloodstream to locate the exact location of the occlusion. The valve is switched to an inflation position such that the balloon is inflated to dilate the vessel. At any point during the process, pressure transducers can be used to measure the bloodstream pressure, contrast fluid pressure, or the inflation fluid pressure.

While there are many inflation syringes on the market that incorporate a pressure gauge/sensor for monitoring high balloon inflation pressure, such syringes are commonly fitted with an analog gauge and, in some cases, a digital readout on the distal end of the syringe body. Since the development of the Hotspur GPS CATH in conjunction with its VisioValve® (Arrow International, Reading, Pa.), a new design incorporating a means for measuring both high and low pressures integrated with a 3-way stopcock is both timely and effective. This new design will allow precise pressure measurement of both high inflation pressure for the balloon (0-30 ATM) and low pressure measurement (0-300 mm Hg) for contrast injection into the blood stream/blood pressure measurement, inter alia. In the present disclosure, the term "3-way stopcock" is synonymous with the term, "3-way valve," unless expressly stated otherwise, or unless dictated otherwise by the context.

The present invention could be integrated onto the distal end of an inflation syringe barrel or be provided as a standalone device containing ports for connecting both the insufflator and contrast syringe. The proposed method allows a physician to use a single insufflator and balloon catheter to measure both intra-balloon and intravascular pressure.

According to embodiments, there is disclosed an apparatus for the treatment of an occluded vessel comprising: a catheter with a proximal end and a distal end and a lumen extending between the proximal and distal end; a balloon disposed on the distal end of the catheter; and, at least a valve; wherein the at least a valve is configured to permit a first fluid to be introduced into the occluded vessel through the lumen and inflation of the balloon by injecting a second fluid through the lumen.

According to embodiments, there is disclosed a valve comprising: an exit port; one or more input ports; and a mechanism capable of switching between more than one stage such that multiple fluids may enter a conduit through the exit port from the one or more input ports.

According to embodiments, there is disclosed a method for dilating a vessel to treat an occlusion of the vessel, the method comprising the steps of: providing an apparatus comprising a catheter having at least a valve with a proximal end and a distal end and a lumen extending between the proximal and distal end, and a balloon disposed on the distal end of the catheter; introducing the catheter into the vessel; injecting a contrast fluid through the lumen into the vessel; directing the catheter to the occlusion; and inflating the balloon by injecting an inflation fluid through the lumen to dilate the vessel at the occlusion.

DETAILED DESCRIPTION

The present disclosure encompasses all possible combinations of the above embodiments, and encompasses all possible disclosures of each independent claim with its dependent claims. For example, what is encompassed is an invention that is the combination of: claim 1+claim 2; or the combination of: claim 1+claim 2+Claim 3; or the combination of claim 1+claim 3+claim 4; or the combination of claim 1+claim 2+claim 3+claim 4; and the like.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent The terms "adapted to," "configured for," and "capable of," mean the same thing. Where more than one of these terms are used in a claim set, it is the case that each and every one of these terms, as they might occur, means, "capable of."

BRIEF DESCRIPTIONS OF THE FIGURES

FIGS. 2A and 2B show a 3-way valve unit.

FIGS. 4A and 4B illustrate a thumb controller.

DETAILED DESCRIPTION OF THE DISCLOSURE

The inventors have developed and discovered novel systems, methods, and designs, relating to smart 3-way valves. The apparatus disclosed herein includes a balloon catheter and a 3-way valve. The particular type of catheter to be used with the valve is the GPS OATH® from Hotspur. This balloon catheter is configured so that in one state fluid introduced into its lumen will enter the vessel and in another state fluid will inflate the balloon to dilate the vessel. The advantage to such a catheter is that separate catheters do not need to be used to perform these separate tasks. Likewise, inflation and pressure measurement are seamlessly linked. The present disclosure encompasses valves, such as those of U.S. Pat. No. 8,043,313 of Krolik et al, which is hereby incorporated by reference in its entirety.

The term "downstream" refers to the direction of flow of a fluid or gas in a tube, conduit, hose, or through a component of a medical device, during ordinary or typical clinical use. Unless specified otherwise, or unless dictated otherwise by context, "downstream" does not refer to the direction of flow of a fluid or gas during non-typical uses, such as during experimental testing or during cleaning of the medical device, where test solutions and cleaning solutions might be used in a direction that is the reverse of the direction in ordinary and typical clinical use.

In embodiments, low pressure sensor, high pressure sensor, or both sensors, are mounted in a position downstream of couplers that are associated with low pressure fluid port and high pressure fluid port, respectively. In another embodiment, low pressure sensor, high pressure sensor, or both sensors, are mounted in a position upstream of the 3-way valve. Alternatively, the low pressure sensor, high pressure sensor, or both sensors are mounted inside the 3-way valve, where the position of mounting is in a location that segregates the low pressure valve from contact with high pressure fluid, and that segregates the high pressure valve from contact with low pressure fluid. In an alternative embodiment, low pressure sensor, high pressure sensor, or both low pressure sensor and high pressure sensor, are mounted upstream of the low pressure port and high pressure port, respectfully, where this mounting is by way of a snap-on module, or a permanently attached module that is exterior to the 3-valve unit, or attached to tube or hose that leads from insufflator to valve unit, or attached to tube or hose that leads from low pressure syringe to valve unit.

Also, the sensor(s) need to be connected to circuit board (most likely surface mounted). Regarding hoses, tubes, pipes, extension lines, and such, these require the ability to tolerate at least 30 ATM of pressure, at least 35 ATM, at least 40 ATM, at least 50 ATM, at least 60 ATM, at least 70 ATM, at least 80 ATM, and so on. In embodiments, the hoses are braid reinforced. In exclusionary embodiments, the present disclosure excludes a medical device, such as a valve or catheter, that is not able to tolerate greater than 30 ATM, that is not able to tolerate greater than 28 ATM, that is not able to tolerate greater than 26 ATM that is not able to tolerate greater than 25 ATM, that is not able to tolerate greater than 20 ATM, that is not able to tolerate greater than 15 ATM, and so on.

In a non-limiting embodiment, the low pressure sensor is damaged when exposed to fluids at pressures greater than 5 atm, greater than 10 atm, greater than 15 atm, greater than 20 atm, greater than 25 atm, greater than 30 atm, and so on. In embodiments, damage occurs with exposure to a fluid under a given pressure for at least 5 seconds, at least 10 seconds, at least 20 seconds, at least 1 minute, at least 2 min, at least 5 min, at least 10 min, at least 20 min, at least 60 min, at least 2 hours, at least 5 hours, at least 10 hours, and so on.

Damage can be assessed, for example, by data demonstrating that the readings given by the low pressure sensor, when used to measure a low pressure fluid, are inaccurate. An inaccurate reading, for example, can be a reading that is greater than 5% greater than the true reading, greater than 10%, greater than 20%, greater than 50%, greater than 100%, greater than 2-fold, than the true reading, and the like. Also, an inaccurate reading can be one that is less than 95% of the true reading, less than 90%, less that 80%, less than 70%, less than 60%, less than 50%, less than 20%, and so on. An inaccurate reading can be one where the low pressure sensor is damaged to the point where it fails to provide any reading.

The following concerns the use of the terms "high pressure fluid" and "low pressure fluid." These terms refer to fluid from the insufflator and from the syringe, respectfully, usually without regard to the actual pressure of these fluids. For example, where the pressure of the "high pressure fluid"

is ramping up, and where its pressure transitions from a relatively low pressure such as atmospheric pressure, to two or three atmospheres, then to 15 or 20 atmospheres, and finally to 25 atmospheres or greater, it is always the case that the same fluid is the "high pressure fluid," unless expressly stated otherwise, or unless dictated otherwise by the context.

Braid reinforced hoses and tubing are available, for example, with braid construction of 2-24 French outer diameter, with braids made of steel, polyester, nylon, nitrinol, and the like, with braids made in the form of round wire or flat wire, with jacket made of PE, PEBA, polyurethane, nylon, with liner made of PTFE, FEP, PE, PEBA, polyurethane, nylon, and so on (Teleflex Medical OEM, Research Triangle Park, N.C.; Merit Medical OEM, South Jordan, Utah; Argon Medical Devices, Plano, Tex.). The present disclosure also provides hoses, tubing, and other components of medical devices, that are rated for high pressure fluids, that do not use braid constructions.

The 3-way valve of the present disclosure is operably linked with a catheter that contains two lumens, one lumen for inflating balloon and the other lumen for delivering a fluid, such as a contrast dye or a therapeutic agent, to the blood vessel lumen. The 3-way valve is housed in a 3-way valve unit, where the unit also includes pressure sensors.

What is included in the 3-way valve unit, is a low pressure sensor for sensing pressure in the lumen of the bloodstream, for example, in the vicinity of an occlusion, and a high pressure sensor, for sensing pressure in the angioplasty balloon. Both pressure sensors are inside the 3-way valve unit, and are in hydraulic communication with the lumen of the bloodstream, and in hydraulic communication with the interior of the balloon.

In alternate embodiments, what is provided is a catheter with more than two lumens, for example, with three, four, or more lumens. In alternative embodiments, what is provided is more than two pressure monitors, for example, three, four, or more pressure monitors, each sensitive to a different region inside, or a different region outside, of the catheter and associated structures.

In exclusionary embodiments, what can be excluded is a device that has only one pressure sensor, or more than two pressure sensors, and so on. In exclusionary embodiments, what can be excluded is a device that has only one lumen, or that has more than two lumens, and the like.

To further reduce the time required to perform the procedure, a valve system has been developed to allow multiple injection means to be attached simultaneously to the valve. In turn, these injection means do not need to be switched in and out for each other when a different fluid needs to be injected into the catheter.

According to embodiments, the at least a valve uses a smart 3-way stopcock in one embodiment. According to embodiments a valve includes 3 ports. The balloon catheter, an insufflator, and a syringe are attached to the ports. The insufflator is used to inflate the balloon and the syringe may be filled with any desired fluid, such as a contrast dye or therapeutic fluid. The user may switch the valve between different positions such that the fluid path is either from the insufflator, the syringe, or closed entirely. Other valve means known in the art are also within the scope of this invention.

According to embodiments, pressure sensors are located in relation to each fluid path. According to embodiments, a high pressure sensor is used to measure the pressure of the balloon upon inflation. A low pressure sensor is used to measure blood pressure or the fluid pressure from the syringe. The valve isolates these sensors from each other to allow for accurate readings of each.

According to embodiments, the valve includes an LCD screen (liquid crystal display) to display various data to the user, such as pressure, position of the valve, and any other desirable information. LED lights (light emitting diode) on the valve indicate the position of the stopcock. One light will turn on to indicate the fluid path from the syringe is in the open position. Another light is used to indicate the fluid path from the insufflator is in the open position. The valve may also include an audible tone, additional LED light, and/or LCD image display to alert the user that an out of range or maximum pressure has been reached in relation to the pressure sensors.

DETAILED DESCRIPTIONS OF THE FIGURES

Figure 1:
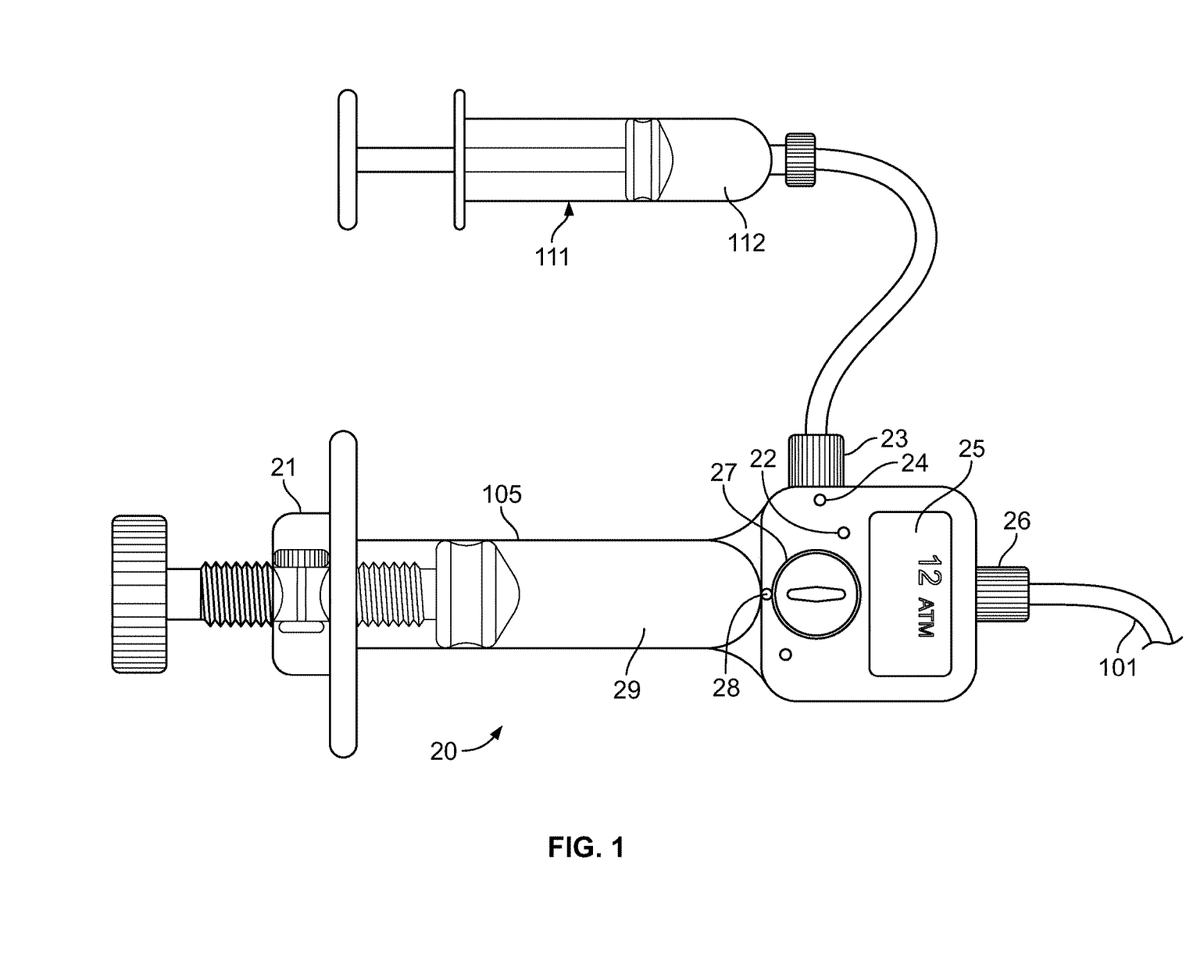
FIG. 1 shows a schematic of embodiments of the instant teachings.

FIG. 1 is a schematic diagram showing the Hotspur GPS CATH® along with the necessary components for inflating balloon (101), injecting contrast and 3-way stopcock (103) for switching the fluid paths between inflation syringe (105) and contrast filled syringe (111), is shown. With this configuration only balloon inflation pressure can be acquired. An alternate configuration (not shown) used by some clinicians eliminates the need for the 3-way stopcock. When using this alternate method inflation syringe (105) and/or contrast filled syringe (111) is connected directly to the Hotspur GPS CATH but requires the clinician to switch syringes pending the procedure step; balloon inflation or contrast injection. This is costly and time-consuming for clinicians and this has not been indicated to be preferred.

FIG. 1 also shows contrast dye (112) in contrast syringe (111), inflation device (20), thread lock (21), LED to indicate flow path (red/green) (22), luer connection (23), low pressure sensor (24), LED display (25) that displays balloon pressure, blood pressure, time, and the like, luer connection (26), 3-way valve (27), high pressure sensor (28), 50% saline/contrast (29), balloon (101), 3-way stopcock (103), and inflation syringe (105). The figure shows devices from, e.g., the Cardiac Care division of Teleflex Medical, Inc., of S.C., Hotspur GPS CATH, inflation syringe, 3-way stopcock, and contrast syringe.

Figure 2A:
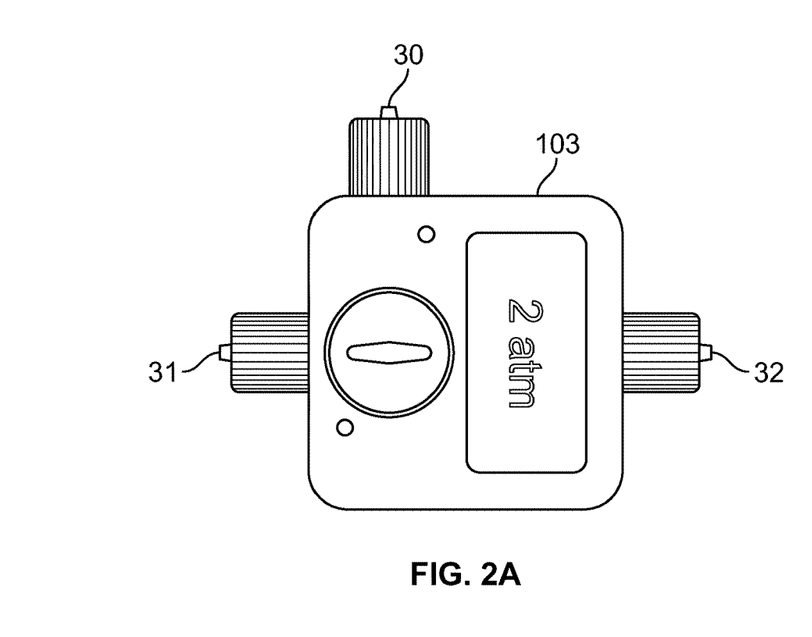
FIG. 2A show ports, and FIG. 2B show internal channels.
Figure 2B:
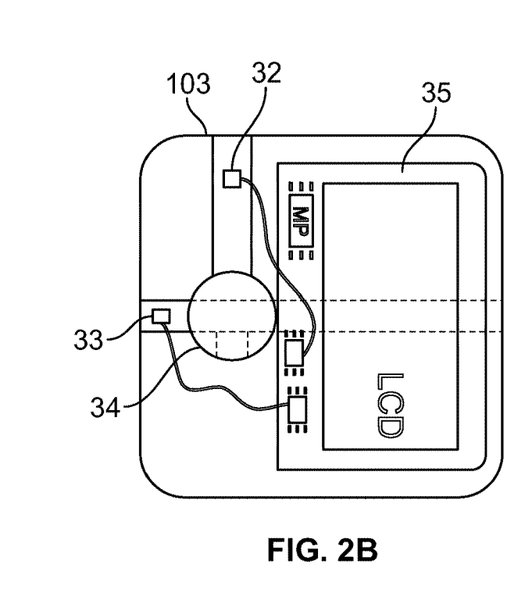

FIG. 2 is a schematic of a standalone device (103) integrated with a smart 3-way stopcock. According to embodiments, a standard inflation syringe and contrast syringe are used in conjunction with the device. Standalone device (103) incorporates all the features as Design 1 with the exception of the insufflator. In this design the insufflator will not be part of the device but supplied separately. Contrast (30), balloon inflation (31), P1 (32), P2 (33), 3-way (34), and board/electronics (35), are shown. Port (30) is low pressure port, for receiving fluid from contrast dye syringe. Port (31) is port for the insufflator. Exit port (32) leads directly to a catheter, that is, a balloon angioplasty catheter. FIG. 2A shows ports, and FIG. 2B shows internal channels. The 3-way valve unit, which contains 3-way stopcock or valve, is integrated with other components, to include, e.g., Hotspur® GPS CATH, inflation syringe, and contrast syringe.

Figure 3A:
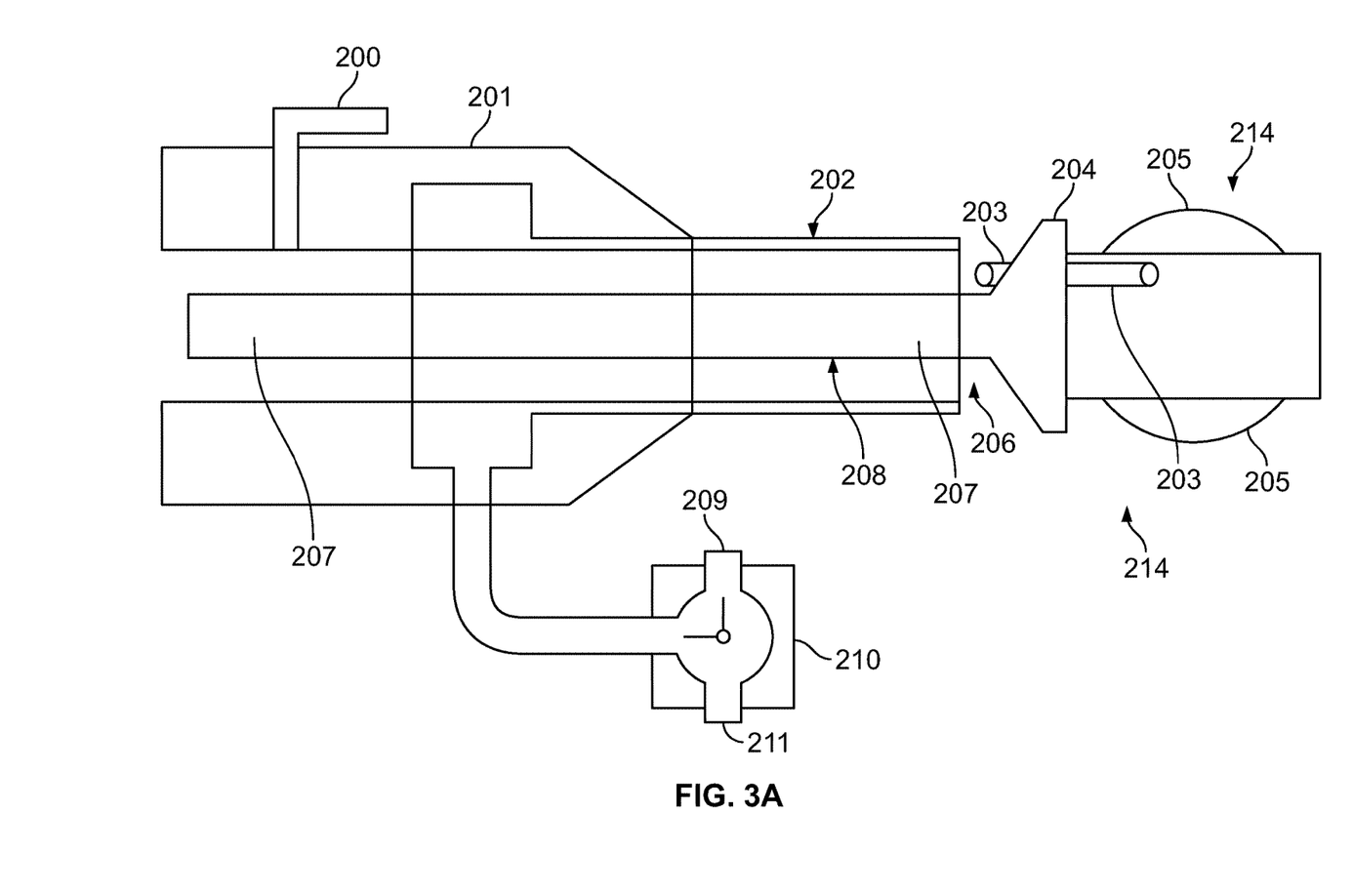
FIG. 3A and FIG. 3B each disclose a valve in open position, resulting in delivery of contrast fluid to vascular lumen.
Figure 3B:
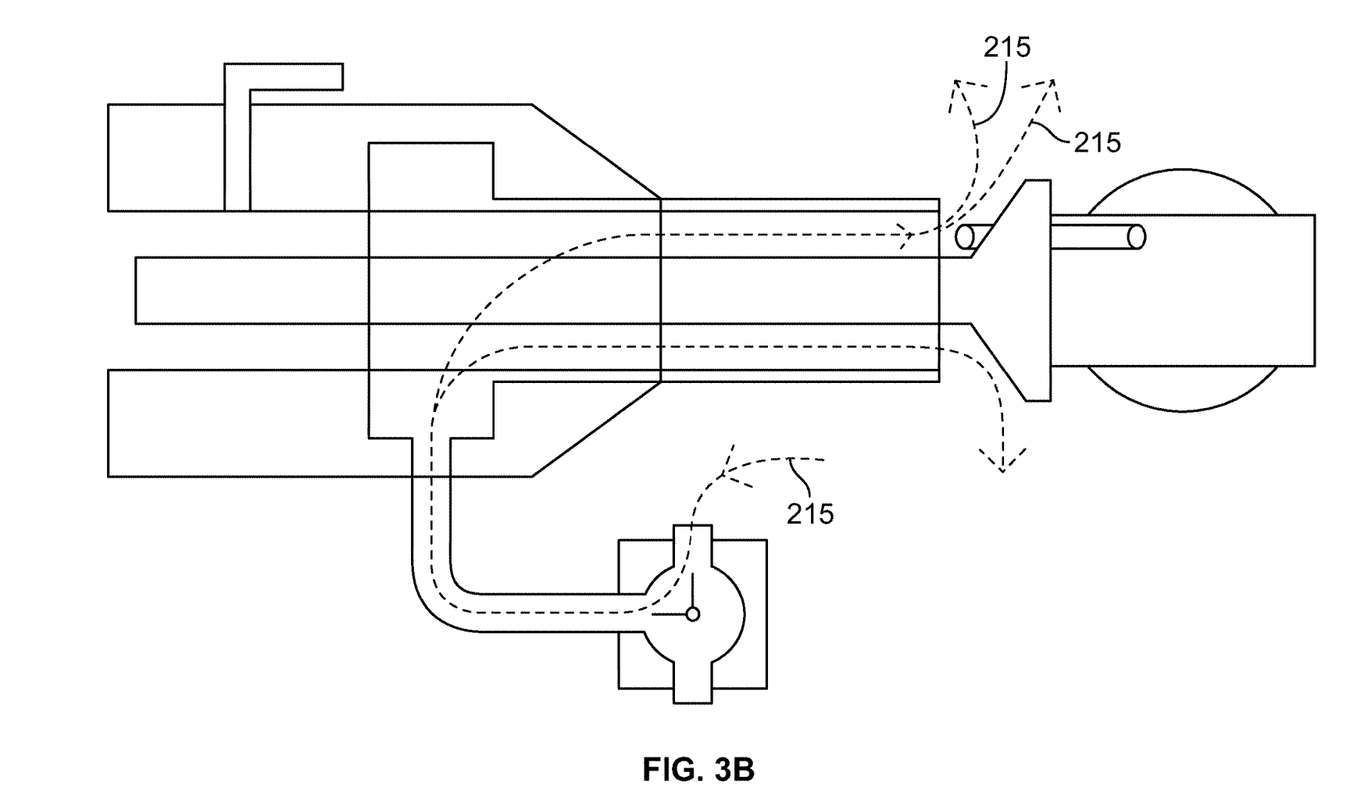
Figure 3C:
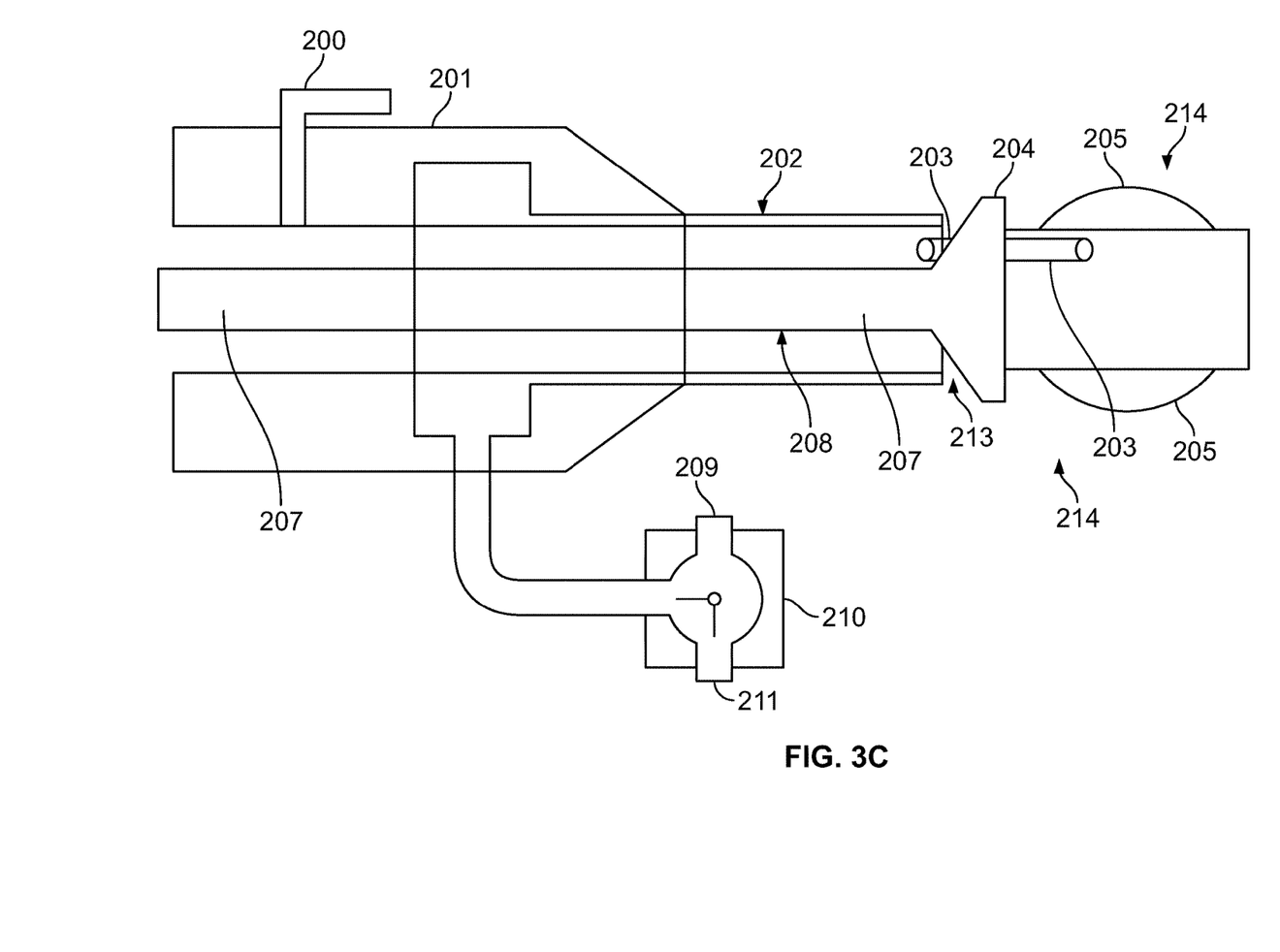
FIG. 3C and FIG. 3D each disclose a valve in closed position, resulting in inflation of balloon.
Figure 3D:
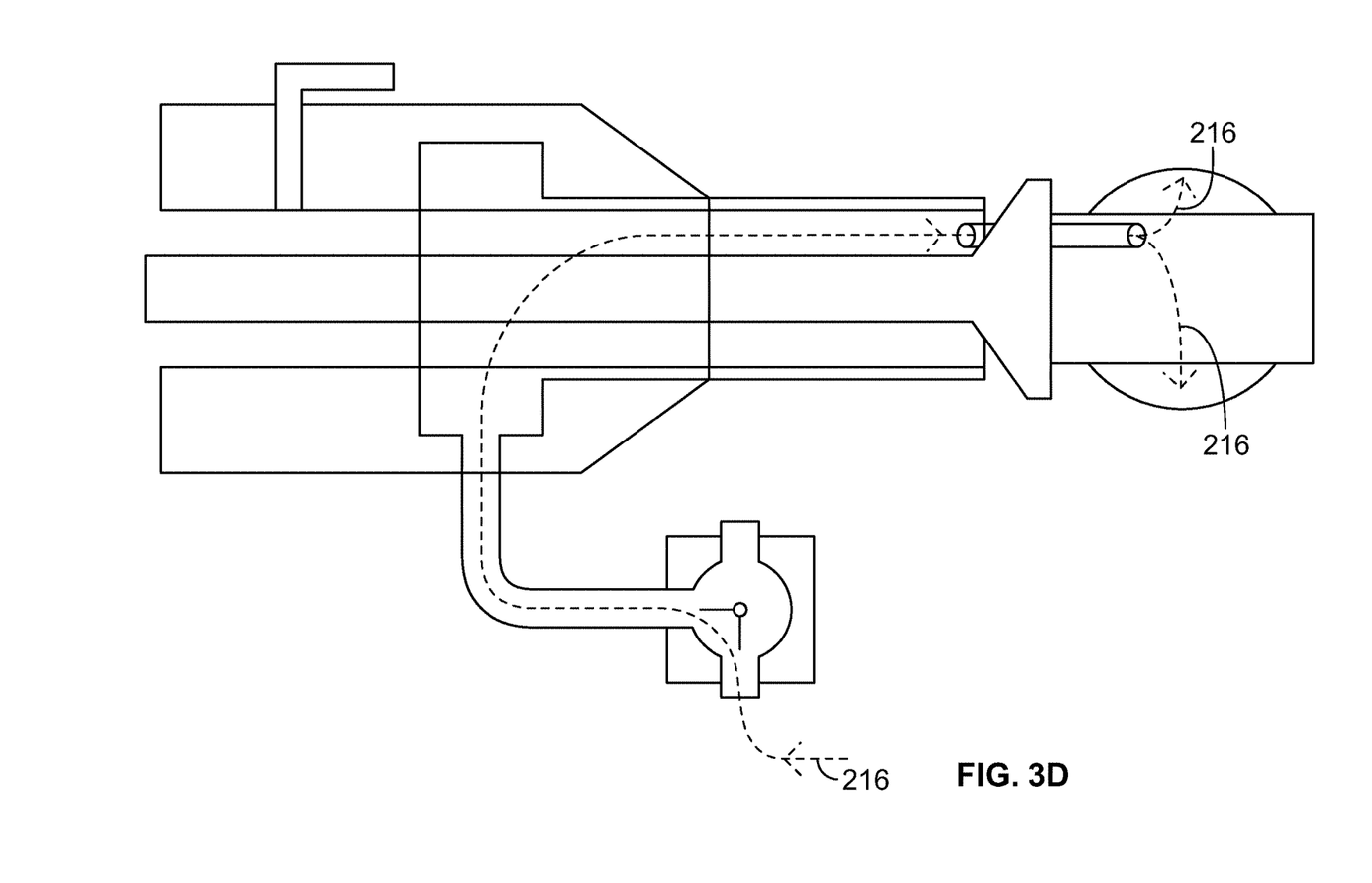

FIG. 3A and FIG. 3B shows valve in open position, resulting in delivery of contrast fluid to vascular lumen. FIG. 3C and FIG. 3D shows valve in closed position, resulting in inflation of balloon. In the open position, the figures show that the longitudinally-moving valve (204) forms a gap (206), where this configuration allows low pressure fluid to enter the vascular lumen. In the closed position, the figures show that the longitudinally-moving valve (204) forms a seal (213) that prevents low pressure fluid from entering the vascular lumen and directs high pressure fluid to the balloon (205). Vascular lumen is indicated by (214).

Thumb controller (200) is operably linked to inner shaft (208). Handle (201) is configured for holding by a clinician. Outer catheter body (202) defines outer catheter lumen, where the outer catheter lumen is configured to direct flow of low pressure fluid (contrast dye; therapeutic agent) to vascular lumen (214). Inflation lumen (203) traverses longitudinally-moving valve (204). The inflation lumen (203) directs high pressure fluid to balloon (205).

In another non-limiting embodiment, diameter of inflation lumen (203) is small and similar to that of a capillary tube, and does not readily facilitate passage of fluids unless the fluids are under a relatively high pressure. Longitudinally-moving valve (204) is shown in open position (FIGS. 3A, B) and in closed position (FIGS. 3C, D). Balloon (205) is angioplasty balloon. Gap (206) is formed when longitudinally-moving valve (204) is in open position. Inner shaft lumen (207) and inner shaft (208) are shown. Inner shaft lumen, optionally, can be used to contain an imaging material for use in proper positioning the medical device. The 3-valve unit (210) includes low pressure fluid port (209) and high pressure fluid port (211). Exit port is disclosed in FIG. 3, and in FIG. 2 has structure number (32).

Distal Terminus of Inner Catheter Body

The distal end (or distal terminus) of inner catheter body (inner shaft) is closed and does not allow fluid communication with vascular lumen. The distal end is closed or blocked in order to ensure that fluid under pressure, as transmitted by inflation lumen, remains under pressure and that pressure is not dissipated by flowing into vascular lumen. Where distal end of inner catheter body has a tubular extension, the distal end of this tubular extension is closed, in order to ensure that high pressure fluid is able to inflate angioplasty balloon. Distal terminus of inner catheter body can be used as a point of attachment of a medical device, such as scraper, a guide member, one or more echogenic apertures, an expandable structure, a helix, a second balloon, a radiopaque member, a supply of releasable therapeutic agent, and so on.

Positions of Pressure Sensors

High and low pressure sensors are located at any point from fluid port (209; 211) to any point that is upstream of the 3-way valve. Pressure sensor can be located at or near the most exterior part of fluid port, or it can be located at a more interior position of the valve unit. In an alternate embodiment, pressure sensor is located within the 3-way valve.

The present disclosure encompasses a valve unit that comprises a plurality of low pressure sensors, that comprises a plurality of high pressure sensors, or that comprises a plurality of both high pressure and low pressure sensors.

Therapeutic agent encompasses, e.g., an anti-cancer agent, anti-proliferative agents, an anti-thrombotic agent, an enzyme, a small molecule, tissue plasminogen activator (tPA), urokinase, streptokinase, an anti-platelet drug such as eptifibatide. Labeled diagnostic agents are encompassed. A composition that is "labeled" is detectable, e.g., by spectroscopic, photochemical, biochemical, immunochemical, isotopic, chemical methods, magnetic resonance imaging (MRI), sonography, and the like. For example, labels include radioactive isotopes of phosphorous, iodine, sulfur, carbon, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

The term "longitudinally moving valve" refers to valves that allow or prevent fluid from outer catheter body lumen to vascular lumen, and where sealing contact of the "fluid-switch valve" with outer catheter body distal prevents fluid flow to vascular lumen, where "longitudinally moving valve" is operably linked to inner shaft, and where longitudinal movement of "longitudinally moving valve" is urged by longitudinal movement of inner shaft. "Longitudinally moving valve" encompasses valve (204), and is not limited to the shape of valve (204). The shape disclosed by structure (204) is exemplary and is not limiting.

The following describes a guidewire embodiment. In a non-limiting, alternate embodiment, inner shaft (208) contains a guidewire. In this guidewire embodiment, it is not the case that the guidewire passes through the inflation lumen.

FIG. 3B shows flow of low pressure fluid (215), and FIG. 3D shows flow of high pressure fluid (216).

Figure 4A:
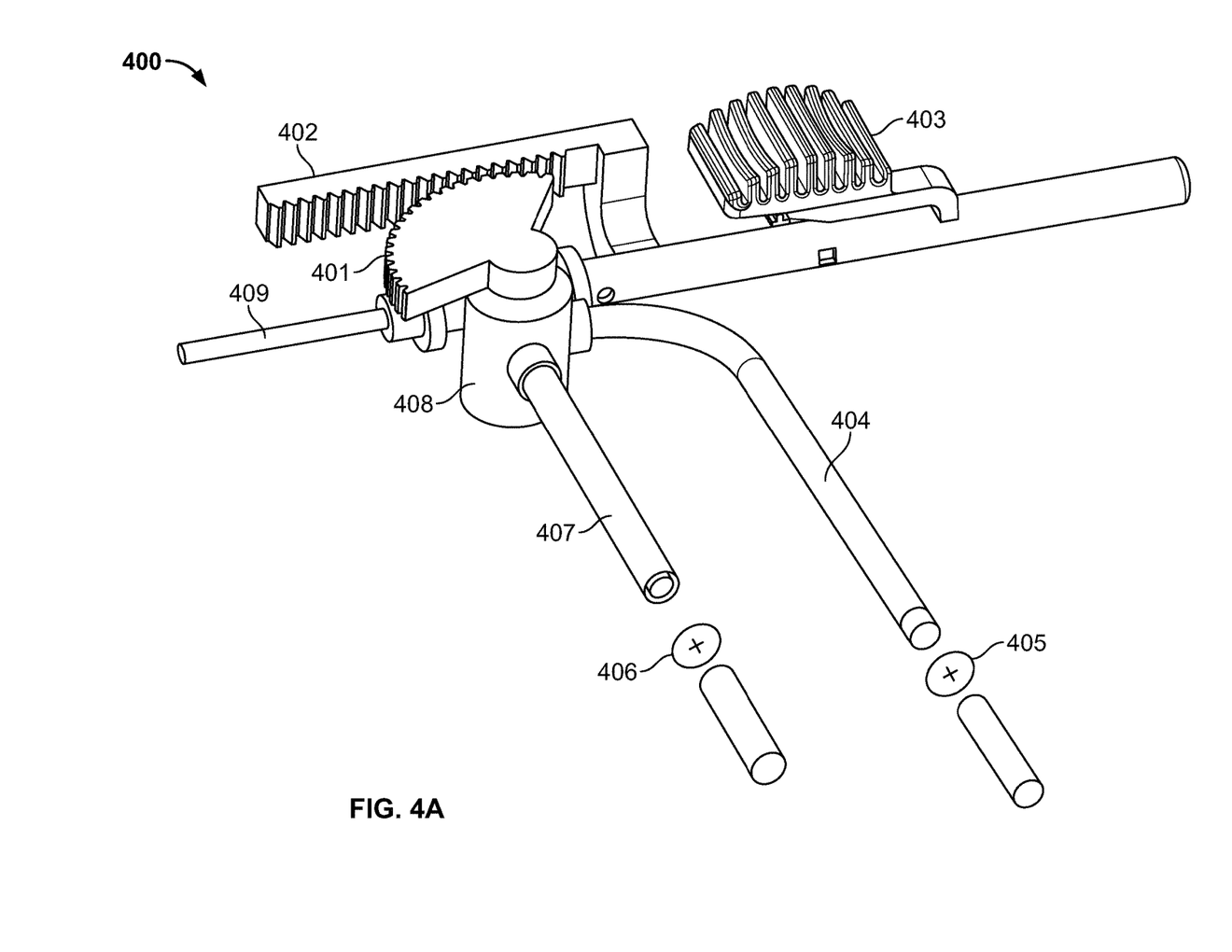
FIG. 4A show an assembled thumb controller, and FIG. 4B show a blow-up of the thumb controller.
Figure 4B:
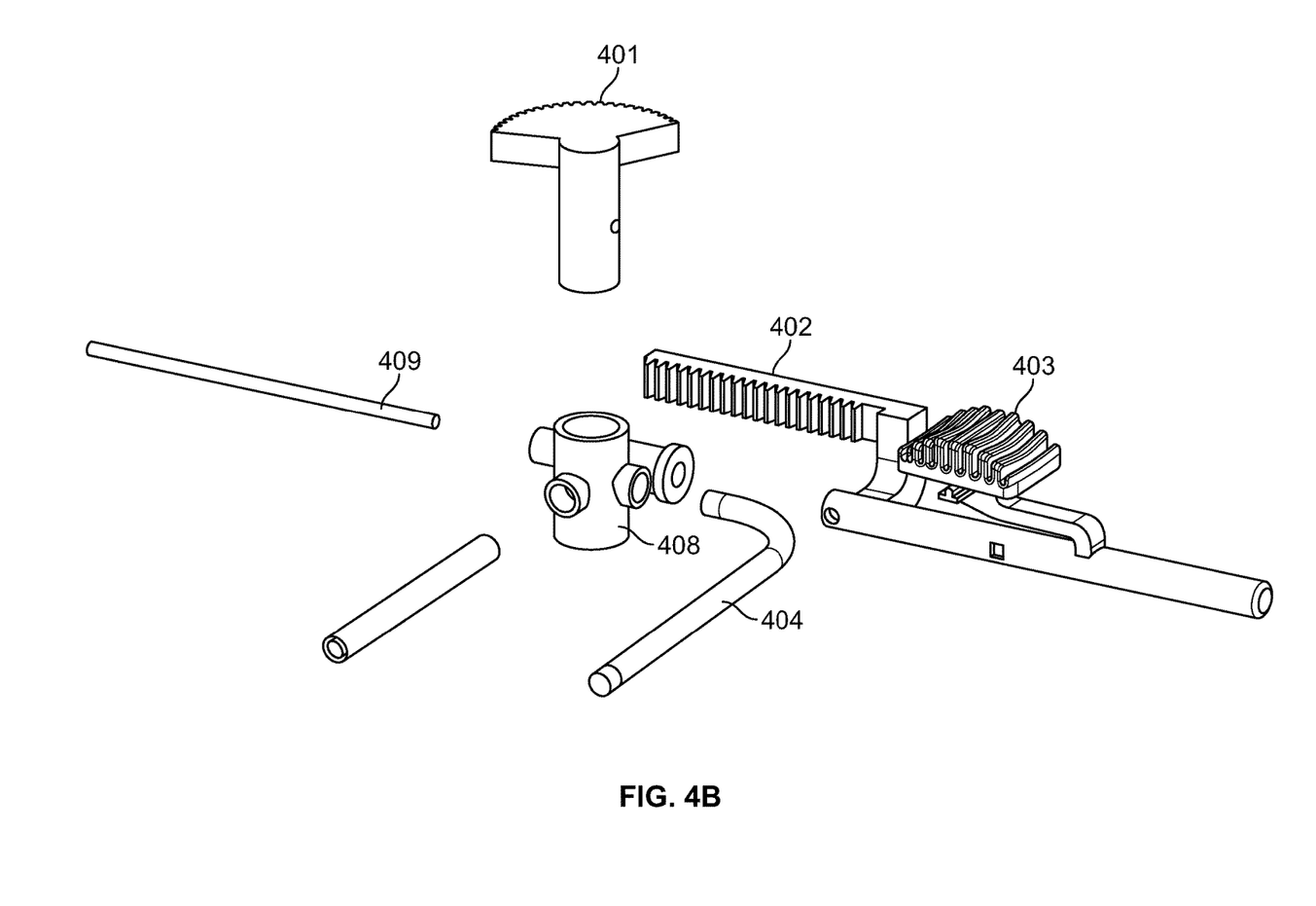

FIG. 4 illustrates thumb controller (400). FIG. 4A shows assembled thumb controller, and FIG. 4B shows a blow-up of the thumb controller. Thumb controller includes a gear rack and spur gear. Thumb controller is operably linked to the 3-way valve. In use, the thumb controller manually reversibly switches the 3-way valve from a position that directs high pressure fluid from insufflator to balloon, to a position that directs low pressure fluid, e.g., contrast fluid or a drug, to vascular lumen.

The handle (201) of the device allows the clinician to easily hold the device, to advance the device in or out of vasculature, and to engage in fine-tuning of position of device in vasculature, while simultaneously permitting the clinician to operate the thumb controller and thereby control deliver of the contrast fluid and the balloon inflation fluid.

Thumb slide (403), contrast fluid line (404), low pressure sensor (405), high pressure sensor (406), insufflator line (407), 3-way valve (408), and 3-way valve (409), are shown. The spur gear can switch the valve by 90 degrees. The rack can be supported within a channel formed within the handle. The two injection ports can exit the same side of the handle. Two extension lines are attached to the stopcock (3-way valve), one for the insufflator and one for contrast fluid injection. In a non-limiting embodiment, the thumb advancer can provide a linear travel of about an inch. The thumb slide switches the two infusion ports from one another.

Regarding control by the thumb controller (400), the thumb controller can be capable of controlling only the 3-way valve (210), it can be capable of controlling only the longitudinally-moving valve (204) (e.g., Visiovalve®), or it can be capable of controlling both the 3-way (210), and the longitudinally-moving valve (204).

The thumb controller is optional, and a similar function can be provided by manual controls that are part of the 3-way valve unit. The present disclosure, in one embodiment, provides controls for switching the 3-way valve only on the 3-way valve unit. In another embodiment, what is provided is controls for switching the 3-way valve only with the thumb controller. In yet another embodiment, manual operation can be with either controls that are part of the 3-way valve unit, or with the thumb controller. The thumb controller automatically switches the 3-way valve as the longitudinally-moving valve (204) is being opened and/or closed. In a but non-limiting embodiment, longitudinally-moving valve (204) can be a Visiovalve®. The valve comprises a body or region that is substantially conical.

Longitudinally-Moving Valve

The longitudinally-moving valve can have a conical region that is configured for an angled fit against outer catheter body distal end. Alternatively, the longitudinally-moving valve can have a flush region that is configured for a flush fit against outer catheter body distal end. In another alternative, the catheter body distal end can have an opening that defines a first hemisphere, and the longitudinally-moving valve can possess a second hemisphere, where the first hemisphere and second hemisphere can fit sealingly together. The sealing fit is reversible, and the fit can be controlled by back or forth longitudinal movement of inner shaft, where movement is relative to outer catheter body.

The conical region is symmetrical about the longitudinal axis of the inner catheter body. In this context, the conical has a proximal narrower portion and a wider distal portion, where the proximal narrower portion is configured to fit sealingly in distal aperture of outer catheter member. The sealing fit is reversible. The conical region has an outer face, and an inner face that defines a conical region lumen. The conical region can be shaped like a cone, in that a cross-section along the longitudinal axis reveals faces that are straight, alternatively, the conical region can be outwardly flared as the bell of a trumpet, or the conical region can be inwardly flared as the bell of a tulip, or the conical region can be partly outwardly flared and partly inwardly flared as is the case with the Liberty Bell, where the general shape is frustroconical.

Structure number (210) of FIG. 3 can be used to refer to both the 3-way valve, as well as to the 3-way valve unit that houses the 3-way valve. The 3-way valve unit includes housing, display, and electronics. Structure number (27) in FIG. 1 is dedicated to referring only to the 3-way valve.

Arrow® GPSCath® can be used for angioplasty with, for example, the femoral, ileac, or renal arteries, and for treating obstructive lesions. Visiovalve® allows physicians to use one catheter to target (locate) the lesion, and also to inflate antioplasty balloon. This valve (the Visiovalve) is located at proximal end of the angioplasty balloon. A medical device that comprises a valve that is the Visiovalve, or a valve that is similar to Visovalve, avoids the need for catheter exchange and avoids the need to re-adjust the guidewire when changing from one mode to another mode. Mode I is balloon inflation. Mode 2 is targeted fluid injection. In a non-limiting embodiment, the valve can be activated on the handle, and switched to allow performance of Mode I or Mode II. Thus, with the Visiovalve, or a similar valve, there is no need to re-establish the position of the guidewire, and there is no need to cross the lesion a second time with the guidewire.

In a non-limiting embodiment, the inner shaft has a closed distal end. In another embodiment, the inner shaft has an open distal end. In a non-limiting embodiment, distal end of inner shaft is connected to proximal end of balloon. In another embodiment, distal portion of inner shaft is connected to balloon, where a substantial part of the longitudinal axis of inflation balloon surrounds the inner shaft. In another embodiment, balloon is connected to only inflation lumen, or to only inner shaft, or to both inflation lumen and to inner shaft. The term "inflation lumen" can refer to a tube, not just to the lumen that is defined by the tube.

Regarding FIG. 1, the disclosure shows an inflation syringe integrated with a smart 3-way stopcock. In this design the stopcock is incorporated onto the distal end of an insufflator. The stopcock can be positioned such that the fluid path is from the insufflator to the Hotspur GPS CATH/balloon or can be switched such that the fluid path is from the contrast syringe to the Hotspur GPS CATH®/Visio-Valve. With this design, the stopcock switches the fluid path as well as isolates the pressure sensors from one another.

The isolation of pressure sensors is necessary due to the pressure differential from the low pressure side contrast syringe/blood pressure measurement and the high pressure side inflation syringe. Exposing the low pressure sensor to the high pressure would be detrimental. Upon switching the device to the desired fluid path an internal sensor will detect the position and trigger an LED light which will inform the user that to which path is open. In addition, this switch will also change the display on LCD screen (107). The screen will indicate the active fluid path, the pressure reading (mm Hg for low pressure side and ATM (atmospheres) for high pressure side) and any additional desired features such as time and or max pressure obtained. An audible tone could also be incorporated as an alert of an out of range condition or max pressure per device label.

According to embodiments, device features include, but are not limited to, the following: A 3-way Stopcock/Switch, 25 cc Syringe Barrel w/Thread Locking Plunger, (i) LCD Screen (ii) LED Indicating Lights, Pressure Transducer (low pressure), Pressure Transducer (high pressure), Audible-Beeper, (iii) Luer Connections. The LED screen, LED indicating lights, LCD screen, beeper, and the like, are optional and are disclosed herein without implying any limitation.

Device features include but not limited to the following: A 3-way Stopcock/Switch, (i) LCD Screen, (ii) LED Indicating Lights, Pressure Transducer (low pressure), Pressure Transducer (high pressure), Audible-Beeper, (iii) Luer Connections, (3) Luer Connections Pressure Sensors The skilled artisan has access to various pressure sensors (see, e.g., Merit Sensor Systems, South Jordan, Utah; Measurement Specialties, Inc., Fremont, Calif.; Miller Instruments, Houston, Tex.; Bullister et al (2002) Artific. Organs. 26:931-938; Giridharan and Skliar (2006) Artific. Organs. 30:301-307; Potkay (2008) Biomed Microdevices. 10:379-392, Kashi, B (November/December 2006) Choosing Sensors for Medical Applications in Passive Component Industry, p. 28-30). The present disclosure provides a valve unit that contains two different pressure sensors that are segregated from each other. The first pressure sensor is for low pressure and the second pressure sensor is for high pressure, where distinct types of sensors are used in order to maximize accuracy in readings, and to prevent fluids under high pressure from damaging the low pressure sensor.

Ports and Hubs

For convenience, the term port, or "fluid port," (30, 31, 32) is used to refer to the apertures leading to and from the 3-way valve. The term "fluid port" can also be used to refer to any connector or hub that is used for connecting to hoses, tubes, fluid lines. The connectors or hubs may reside in a recess located in the wall of the 3-way valve unit, or they may protrude from the exterior surface of the 3-way valve unit. In an embodiment, low pressure syringe and insufflator are reversibly connected to valve unit by way of coupler or hub. In an alternate embodiment, low pressure syringe and insufflator are permanently connected to valve unit, and here there is a need for port, but not a need for a coupler or hub.

The hub can take the form of a coupler, it can comprise a coupler, or it can consist of a coupler. Couplers involving rotatably engaging studs and complimentary slots, slots in channels, tapered fits, exterior clips, and ring and collar mechanisms, are available (see, e.g., U.S. Pat. No. 6,336,914 of Gillespie; U.S. Pat. No. 4,609,370 of Morrison; US 2010/0204654 of Mulholland; US 2007/0123825 of King and Wortley; U.S. Pat. No. 6,663,595 of Spohn and Dinsmore; US2008/0262430 of Anderson et al; U.S. Pat. No. 5,885,217 of Gisselberg; and US 2005/0090779 of Osypka, each of which is incorporated herein in its entirety. Storz-type couplers are available (see, U.S. Pat. No. 489,107 of Storz, U.S. Pat. No. 6,695,816 of Casidy; U.S. Pat. No. 4,648,630 of Bruch, and U.S. Pat. No. 7,128,091 of Istre, each of which is incorporated herein in its entirety).

While the method and apparatus have been described in terms of what are presently considered to be the more practical embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC § 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A valve unit configured to direct a high pressure fluid and low pressure fluid to a catheter, the catheter comprising a balloon having a balloon lumen that receives the high pressure fluid, and the catheter further comprising a vascular lumen that receives the low pressure fluid, the valve unit comprising:
   a housing;
   a high pressure fluid port for receiving the high pressure fluid, a low pressure fluid port for receiving the low pressure fluid, and an exit port extending through the housing for transmitting the high pressure fluid or the low pressure fluid to the catheter, the high pressure fluid being different from the low pressure fluid;
   a 3-way valve within the housing and in fluid communication with the high pressure fluid port, the low pressure fluid port, and the exit port, wherein:
      the 3-way valve has a first position to receive high pressure fluid via the high pressure fluid port and to transmit the high pressure fluid through the exit port downstream to the balloon lumen of the catheter to inflate the balloon,
      the 3-way valve has a second position to receive low pressure fluid via the low pressure fluid port and to transmit the low pressure fluid through the exit port downstream to the vascular lumen of the catheter, and
      the 3-way valve has a third position to simultaneously prevent flow of the high pressure fluid from the high pressure fluid port to the exit port and flow of the low pressure fluid from the low pressure fluid port to the exit port;
   a high pressure sensor within the housing and configured to detect pressure of the high pressure fluid, wherein the high pressure sensor does not contact the low pressure fluid; and
   a low pressure sensor within the housing and configured to detect pressure of the low pressure fluid or pressure within a lumen of the bloodstream in which the catheter resides, wherein the low pressure sensor does not contact the high pressure fluid, and wherein the low pressure sensor is different from the high pressure sensor.

2. The valve unit of claim 1, wherein the balloon is an angioplasty balloon.

3. The valve unit of claim 1, wherein:
the low pressure sensor is located upstream of the 3-way valve,
the high pressure sensor is located upstream of the 3-way valve, or
both the low pressure sensor and the high pressure sensor are located upstream of the 3-way valve.

4. The valve unit of claim 1, wherein the low pressure fluid comprises a contrast agent, a therapeutic agent, or a combination thereof.

5. The valve unit of claim 1, wherein the catheter further comprises:
a valve that is configured to seal a distal end of the catheter to prevent fluid flow to the lumen of the bloodstream,
wherein the balloon lumen passes through the valve, and is configured to receive the high pressure fluid when the valve seals the distal end of the catheter.

6. The valve unit of claim 1, further comprising a thumb slide operably linked to the 3-way valve, wherein the thumb slide is configured to adjust the 3-way valve between the first position, the second position and the third position.

7. The valve unit of claim 5, further comprising a thumb slide operably linked to the valve, wherein proximal to distal movement of the thumb slide opens the valve, and distal to proximal movement of the thumb slide closes the valve.

8. The valve unit of claim 1, further comprising a low pressure fluid syringe, an insufflator, or a combination thereof.

9. The valve unit of claim 1, further comprising:
a display within the housing, the display being configured to display the pressure detected by the low pressure sensor and by the high pressure sensor.

10. The valve unit of claim 1, wherein the high pressure fluid is under a pressure of 30 atmospheres.

11. The valve unit of claim 1, further comprising:
an insufflator or high pressure syringe in fluid communication with the high pressure fluid port, and
a low pressure syringe in fluid communication with the low pressure fluid port.

12. The valve unit of claim 1, further comprising:
an indicator within the housing, the indicator being configured to visually indicate when the 3-way valve is receiving high pressure fluid and when the 3-way valve is receiving low pressure fluid.

13. The valve unit of claim 12, wherein the indicator is a light-emitting diode.

14. The valve unit of claim 5, wherein the valve is a longitudinally moving valve.

15. The valve unit of claim 12, further comprising a display within the housing, the display being configured to display the pressure detected by the low pressure sensor and by the high pressure sensor.

16. The valve unit of claim 4, wherein the high pressure fluid comprises saline.

* * * * *